United States Patent [19]
Gustavsson et al.

[11] Patent Number: 5,942,624
[45] Date of Patent: Aug. 24, 1999

[54] MANUFACTURING PROCESS FOR FELODIPINE

[75] Inventors: Anders Gustavsson, Nykvarn; Åke Källström; Sven Palmér, both of Södertälje, all of Sweden

[73] Assignee: Astra Aktiebolag, Sodertalje, Sweden

[21] Appl. No.: 08/750,933

[22] PCT Filed: Dec. 13, 1996

[86] PCT No.: PCT/SE96/01649

§ 371 Date: Feb. 13, 1997

§ 102(e) Date: Feb. 13, 1997

[87] PCT Pub. No.: WO97/25313

PCT Pub. Date: Jul. 17, 1997

[30] Foreign Application Priority Data

Jan. 10, 1996 [SE] Sweden .................................. 9600086

[51] Int. Cl.$^6$ .................................................. C07D 211/86
[52] U.S. Cl. ............................................................ 546/321
[58] Field of Search ............................................. 546/321

[56] References Cited

U.S. PATENT DOCUMENTS 5,310,917  5/1994  Auerbach ................................ 546/249

FOREIGN PATENT DOCUMENTS 0007293  1/1980  European Pat. Off. .
2508181  9/1976  Germany .

*Primary Examiner*—Jane Fan
*Attorney, Agent, or Firm*—White & Case L.L.P.

[57] ABSTRACT

A method for the manufacture of felodipine by reaction of dichlorobenzylidene and ethyl 3-aminocrotonate using an alcohol as solvent.

12 Claims, No Drawings

MANUFACTURING PROCESS FOR FELODIPINE

This is a 371 of PCT/SE96/01649 filed Dec. 13, 1996 now WO97/25313 issued Jul. 19, 1997

FIELD OF THE INVENTION

The present invention relates to an improved method for the manufacture of felodipine (ethyl methyl 4-(2,3-dichlorophenyl)-1,4-dihydro-2,6-dimethyl-3,5-pyridine-dicarboxylate) via the route of reacting 2,3-dichlorobenzylideneacetylacetic acid-methylester (in the following dichlorobenzylidene for short) with ethyl 3-aminocrotonate.

PRIOR ART

EP 7293 discloses a method for the preparation of felodipine using dichlorobenzylidene and ethyl 3-aminocrotonate as starting materials. The solvent used is tertiary butanol. No catalyst is used. The reaction time is long, that is 90 minutes or more.

U.S. Pat. No. 5,310,917 discloses a method for the preparation of felodipine using dichlorobenzylidene and ethyl 3-aminocrotonate as starting materials. The solvent used is ethanol.

DISCLOSURE OF THE INVENTION

It has now been found that felodipine, which is a calcium-channel blocker, can be prepared in a manner that is fast, environmentally sound and gives a good yield using starting materials that are known per se. The new method uses pyridine as a catalyst in combination with an alcohol as solvent The method is described by the reaction scheme below:

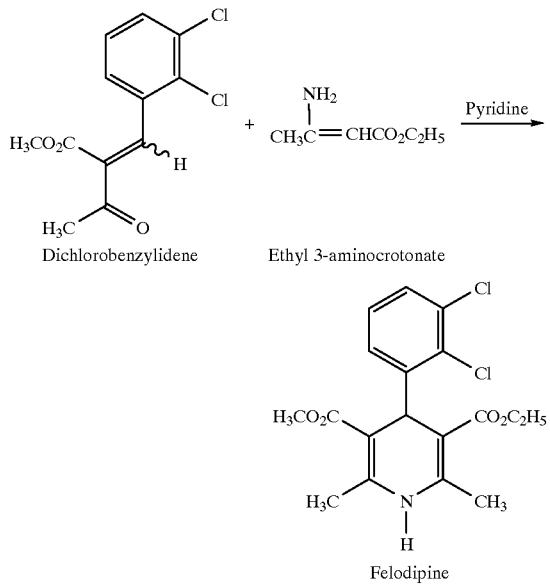

Felodipine

Dichlorobenzylidene is reacted with ethyl 3-aminocrotonate in the presence of pyridine in refluxing alcohol, such as methanol, ethanol or propanol, preferably ethanol. Preferably, the alcohol is then evaporated at reduced pressure and ethyl acetate or methylene chloride is added. The solution can be purified by acidic and neutral aqueous extractions. The solvent can be removed by evaporation. The product can be dissolved in acetone or diisopropyl ether, crystallized by cooling, isolated by filtration and finally washed with acetone, or diisopropyl ether.

Dichlorobenzylidene is reacted with ethyl 3-aminocrotonate (0.5–0.9 g/g dichlorobenzylidene, preferably 0.58–0.60 g/g dichlorobenzylidene). The reactants are charged together with the solvent alcohol (preferably ethanol 2.5–4.8 ml/g, preferably 3.2–3.9 ml ethanol/g dichlorobenzylidene) and the catalyst pyridine (0.03–0.2 ml/g dichlorobenzylidene, preferably 0.035–0.045 g/g dichlorobenzylidene).

Preparation of dichlorobenzylidene starting material

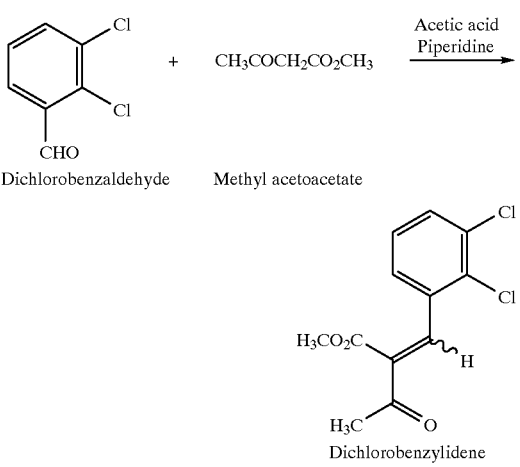

2,3-Dichlorobenzaldehyde    Methyl acetoacetate

Dichlorobenzylidene 2,3-Dichlorobenzaldehyde is reacted with methyl acetoacetate in a suitable solvent in the presence of a catalytic amount of acetic acid and piperidine. Water is azeotropically separated off during the reaction. The reaction mixture is extracted in order to remove the catalysts. The solvent is evaporated and methanol is added. The product is crystallized by cooling the solution, isolated by filtration and finally washed with methanol.

Working examples

Example 1

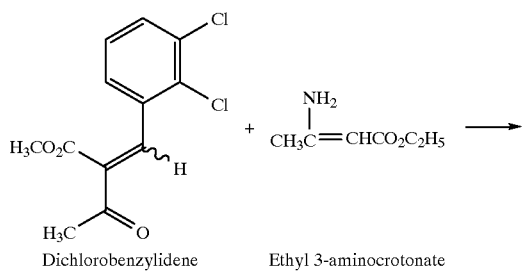

Dichlorobenzylidene    Ethyl 3-aminocrotonate

-continued

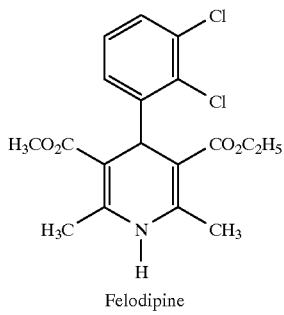
Felodipine 35.3 g of dichlorobenzylidene was reacted with 20.7 g of ethyl 3-aminocrotonate in the presence of 1.3 g of pyridine in refluxing ethanol (91 ml). Ethanol was evaporated under reduced pressure and ethyl acetate (195 ml) was added in order to dissolve the residue. The solution was purified by acidic extraction (7.3 g of (HCl (aqeous) in 30 ml of $H_2O$). The solvent was evaporated and acetone (116 ml) was added. The product was crystallized by cooling the solution to −10° C., isolated by filtration and washed with acetone. Yield: Approximately 85

Example 2

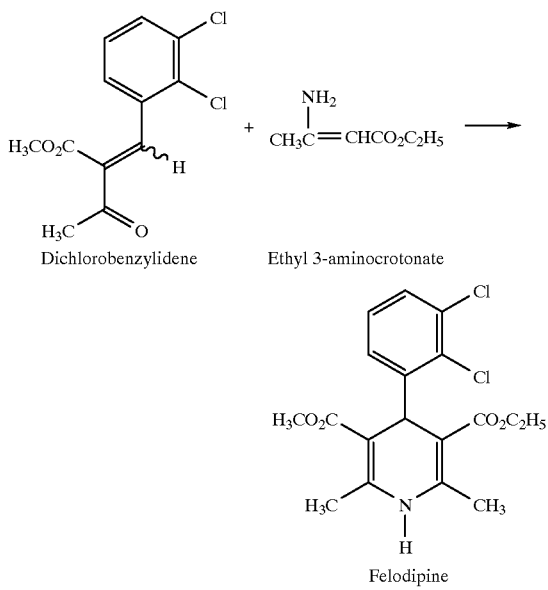

30.3 g of dichlorobenzylidene was reacted with 17.8 g of ethyl 3-aminocrotonate in the presence of 5.9 g of pyridine in refluxing ethanol (94 ml). Ethanol was evaporated under reduced pressure and 118 ml of methylene chloride was added. The solution was purified by acidic extraction (6.3 g of HCl (aqeous) in 24 ml of $H_2O$). The methylene chloride phase was treated with 3 g of sodium sulphate (anhydrous) in order to remove the residues of water. The solvent was evaporated and 85 ml of diisopropyl ether was added. The product was crystallized by cooling the solution to 0° C., isolated by filtration and washed with diisopropyl ether. Yield: Approximately 85%

We claim:

1. A method for the manufacture of felodipine, characterized by reacting 2,3-dichlorobenzylideneacetylacetic acid-methylester with ethyl 3-aminocrotonate in refluxing alcohol in the presence of pyridine as catalyst.

2. A method according to claim 1 wherein the alcohol is ethanol.

3. A method according to any of claims 1–2 wherein the obtained felodipine is taken up into a solution.

4. A method according to claim 3 wherein the obtained felodipine is taken up into ethyl acetate.

5. A method according to claim 3 wherein the obtained felodipine is taken up into methylene chloride.

6. A method according to any of claims 1–2 wherein the obtained felodipine is purified by crystallization.

7. A method according to claim 6 wherein the crystallization is performed from acetone.

8. A method according to claim 6 wherein the crystallization is performed from diisopropyl ether.

9. A method according to any of the preceding claims, wherein the amount of ethyl 3-aminocrotonate is 0.5–0.9 g per g of 2,3-dichlorobenzylideneacetylacetic acid-methylester.

10. A method according to any of the preceding claims, wherein the amount of ethanol is 2.5–4.8 ml per g of 2,3-dichlorobenzylideneacetylacetic acid-methylester.

11. A method according to any of the preceding claims, wherein the amount of pyridine is 0.03–0.2 ml per g of 2,3-dichlorobenzylideneacetylacetic acid-methylester.

12. A method according to claim 6 wherein the purified felodipine is admixed with an excipient, diluent or carrier.

* * * * *